(12) United States Patent
Asano

(10) Patent No.: US 12,046,117 B2
(45) Date of Patent: Jul. 23, 2024

(54) GAS DETECTION DEVICE, GAS DETECTION METHOD, AND GAS DETECTION PROGRAM

(71) Applicant: Konica Minolta, Inc., Tokyo (JP)

(72) Inventor: Motohiro Asano, Osaka (JP)

(73) Assignee: KONICA MINOLTA, INC., Tokyo (JP)

( * ) Notice: Subject to any disclaimer, the term of this patent is extended or adjusted under 35 U.S.C. 154(b) by 367 days.

(21) Appl. No.: 17/440,516

(22) PCT Filed: Dec. 6, 2019

(86) PCT No.: PCT/JP2019/047950
§ 371 (c)(1),
(2) Date: Sep. 17, 2021

(87) PCT Pub. No.: WO2020/188905
PCT Pub. Date: Sep. 24, 2020

(65) Prior Publication Data
US 2022/0189279 A1   Jun. 16, 2022

(30) Foreign Application Priority Data

Mar. 19, 2019   (JP) .................... 2019-050850

(51) Int. Cl.
*G08B 21/12* (2006.01)
*G01N 33/00* (2006.01)
(Continued)

(52) U.S. Cl.
CPC ......... *G08B 21/12* (2013.01); *G01N 33/0027* (2013.01); *G06V 10/25* (2022.01);
(Continued)

(58) Field of Classification Search
CPC ...... G08B 21/12; G06V 10/25; G06V 10/987; G06V 20/52; G06V 10/267; G06V 10/273; G06V 10/945; G01N 33/0027
See application file for complete search history.

(56) References Cited

U.S. PATENT DOCUMENTS

2004/0032494 A1 * 2/2004 Ito .................... G08B 13/19606
348/169

FOREIGN PATENT DOCUMENTS

JP           62222394 A  *  9/1987
JP           S62222394 A     9/1987
(Continued)

OTHER PUBLICATIONS

International Search Report for International Application No. PCT/JP2019/047950; Date of Mailing: Feb. 10, 2020.
(Continued)

*Primary Examiner* — Wednel Cadeau
(74) *Attorney, Agent, or Firm* — CANTOR COLBURN LLP

(57) ABSTRACT

A gas detection device, a gas detection method, and a gas detection program according to the present invention detect gas on the basis of an image obtained by imaging a detection target. The gas detection device, the gas detection method, and the gas detection program; generated accumulated data obtained by accumulating a number of times of gas detection in a predetermined unit of accumulation, on the basis of a plurality of images captured at a plurality of times different from each other in a predetermined period; and generate a mask image for suppressing notification of detected gas on the basis of the generated accumulated data.

17 Claims, 15 Drawing Sheets

(51) Int. Cl.
　　　*G06V 10/25*　　　(2022.01)
　　　*G06V 10/26*　　　(2022.01)
　　　*G06V 10/94*　　　(2022.01)
　　　*G06V 10/98*　　　(2022.01)
　　　*G06V 20/52*　　　(2022.01)
(52) U.S. Cl.
　　　CPC .......... *G06V 10/267* (2022.01); *G06V 10/273* (2022.01); *G06V 10/945* (2022.01); *G06V 10/987* (2022.01); *G06V 20/52* (2022.01)

(56) References Cited

FOREIGN PATENT DOCUMENTS

| | | | | |
|---|---|---|---|---|
| JP | 09016254 | A | * | 1/1997 |
| JP | H0916254 | A | | 1/1997 |
| JP | 2004096742 | A | | 3/2004 |
| JP | 2008271329 | A | * | 11/2008 |
| JP | 2008271329 | A | | 11/2008 |
| JP | 6245418 | B2 | | 12/2017 |
| WO | 2017073430 | A1 | | 5/2017 |

OTHER PUBLICATIONS

PCT Written Opinion of the International Searching Authority for International Application No. PCT/JP2019/047950; Date of Mailing: Feb. 10, 2020.

\* cited by examiner

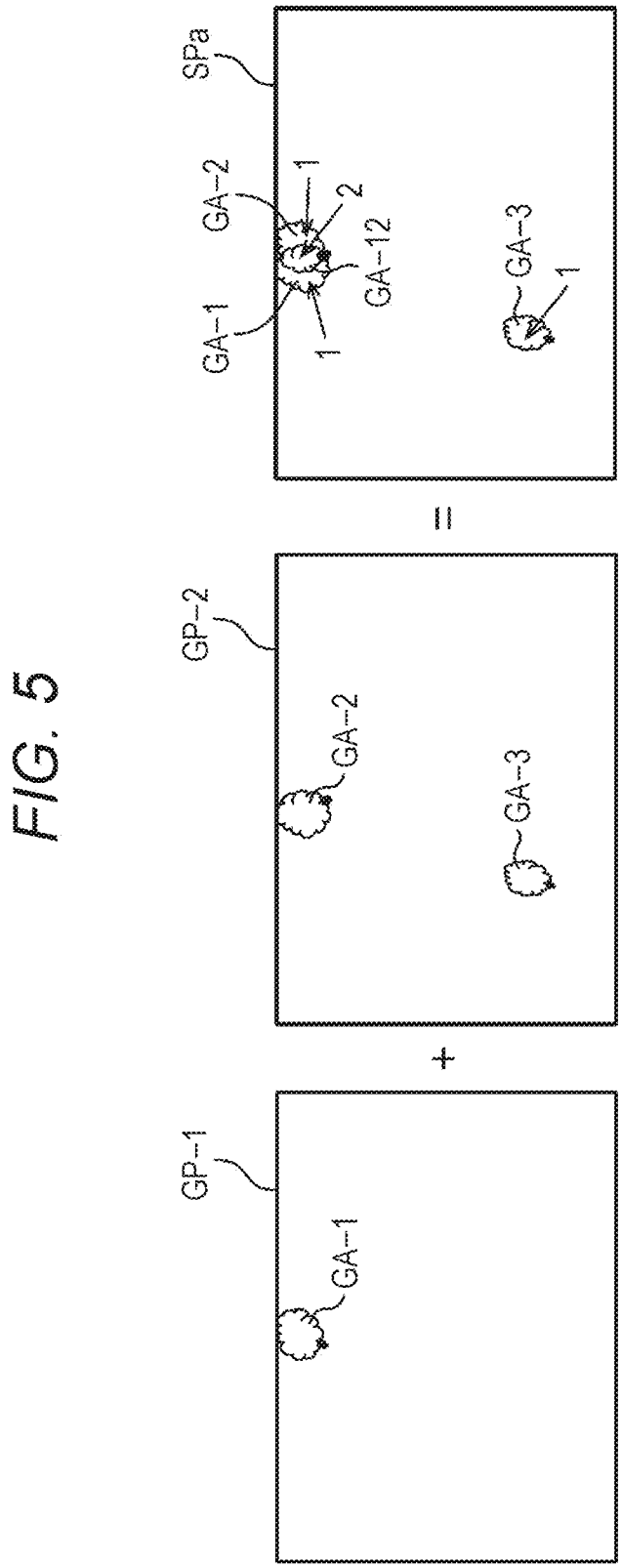

FIG. 6A
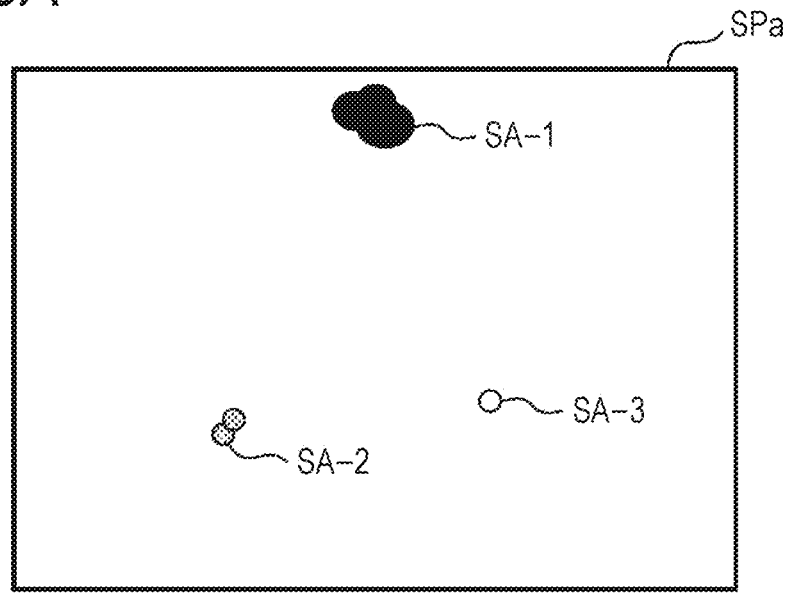
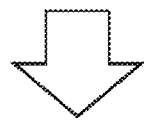
FIG. 6B
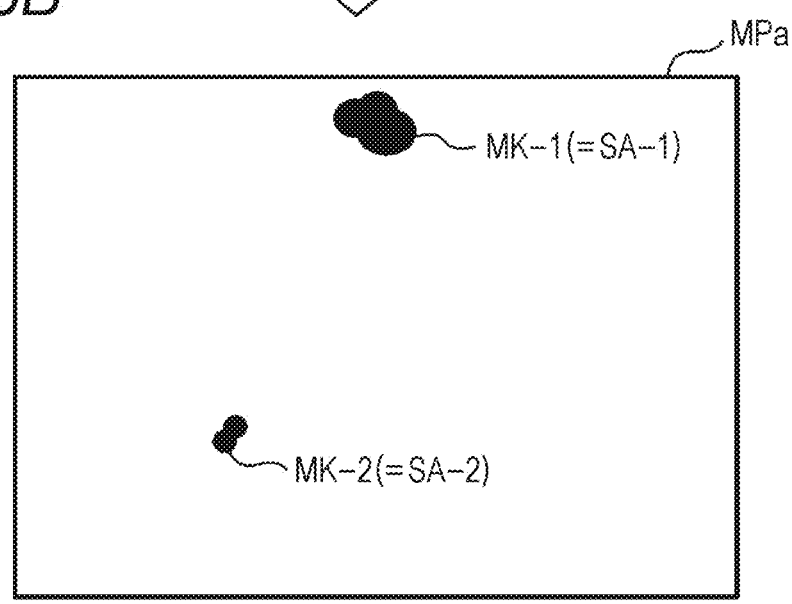

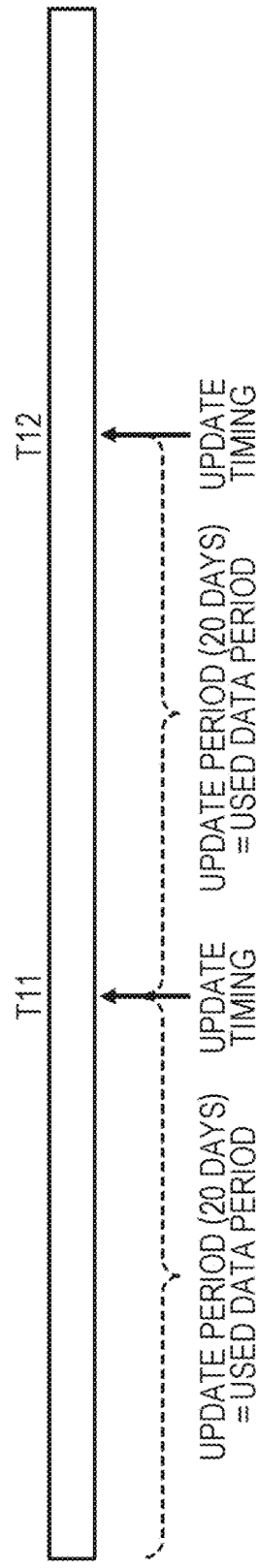
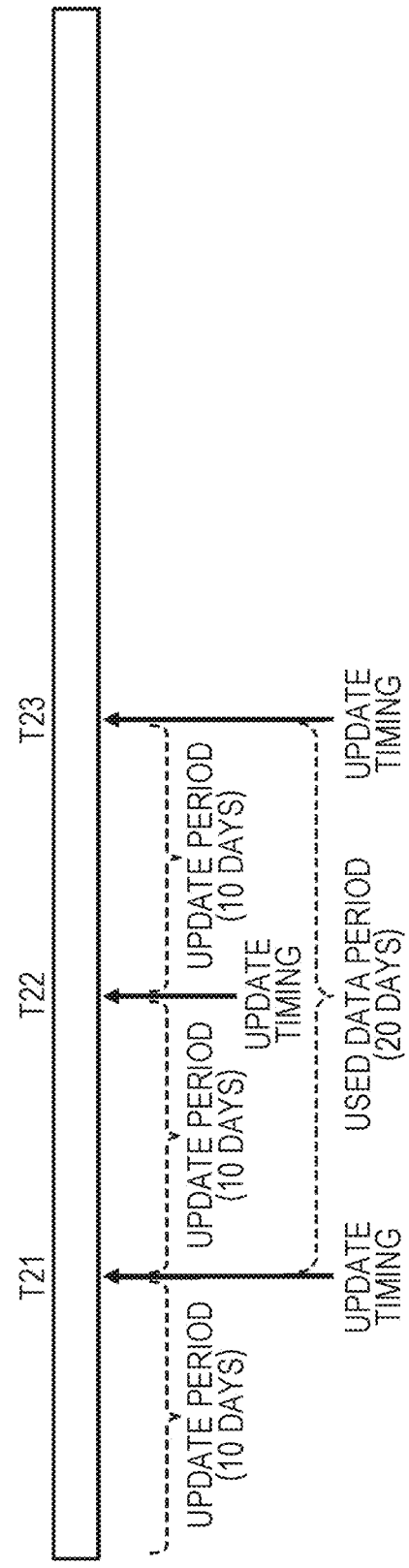

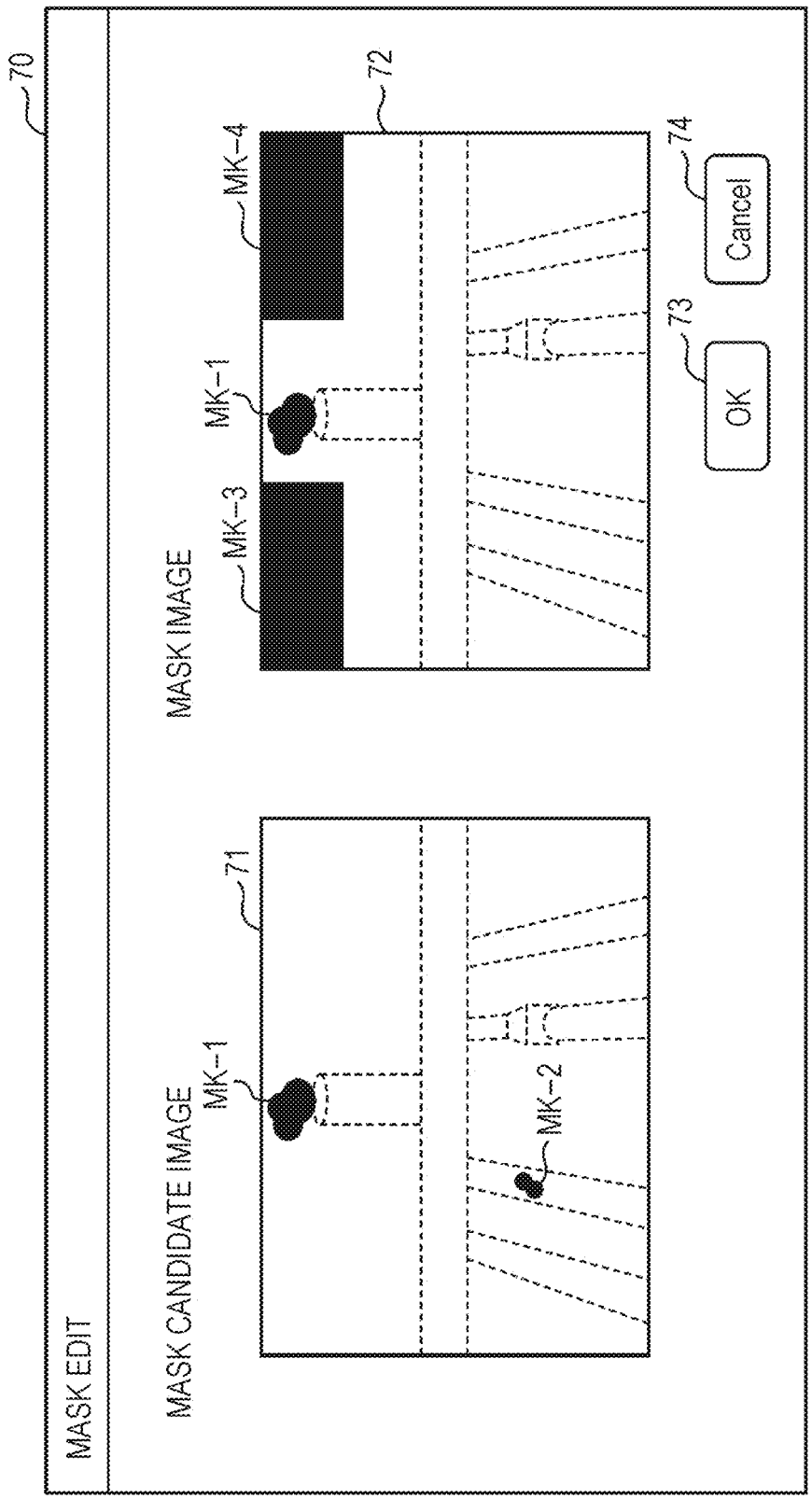

FIG. 12A
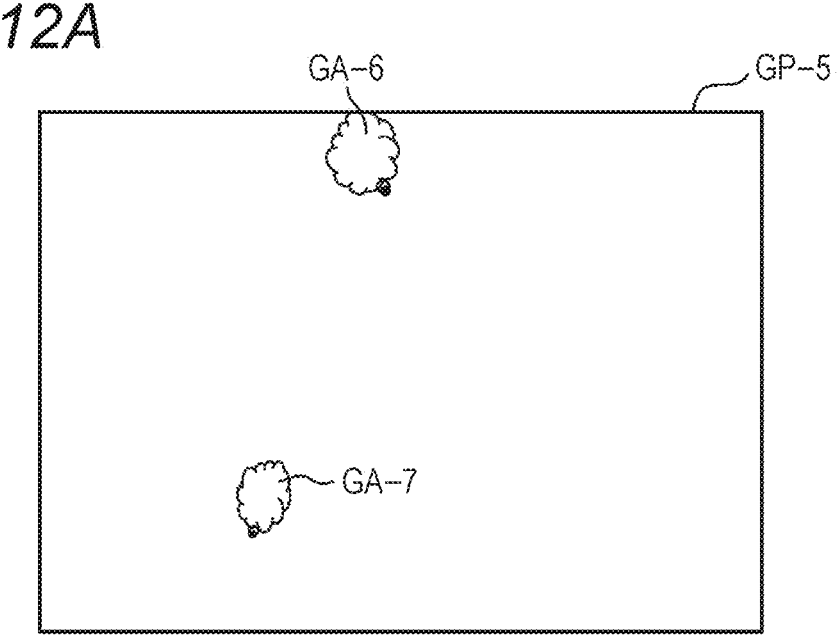
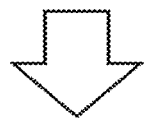 BARYCENTRIC POSITION IS CALCULATED
FIG. 12B
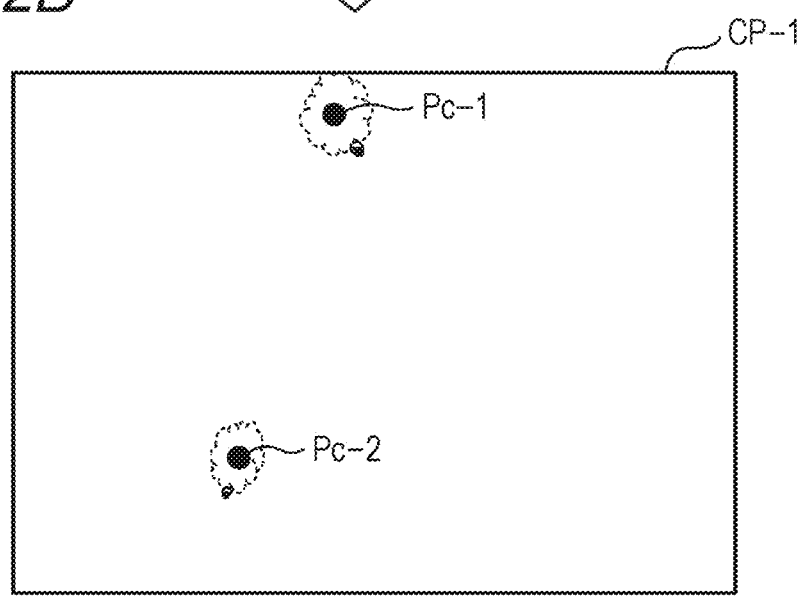

FOR "0 TO 2 O'CLOCK"  MP-1(MPa-1,MPb-1)

FOR "9 TO 11 O'CLOCK"  MP-2(MPa-2,MPb-2)

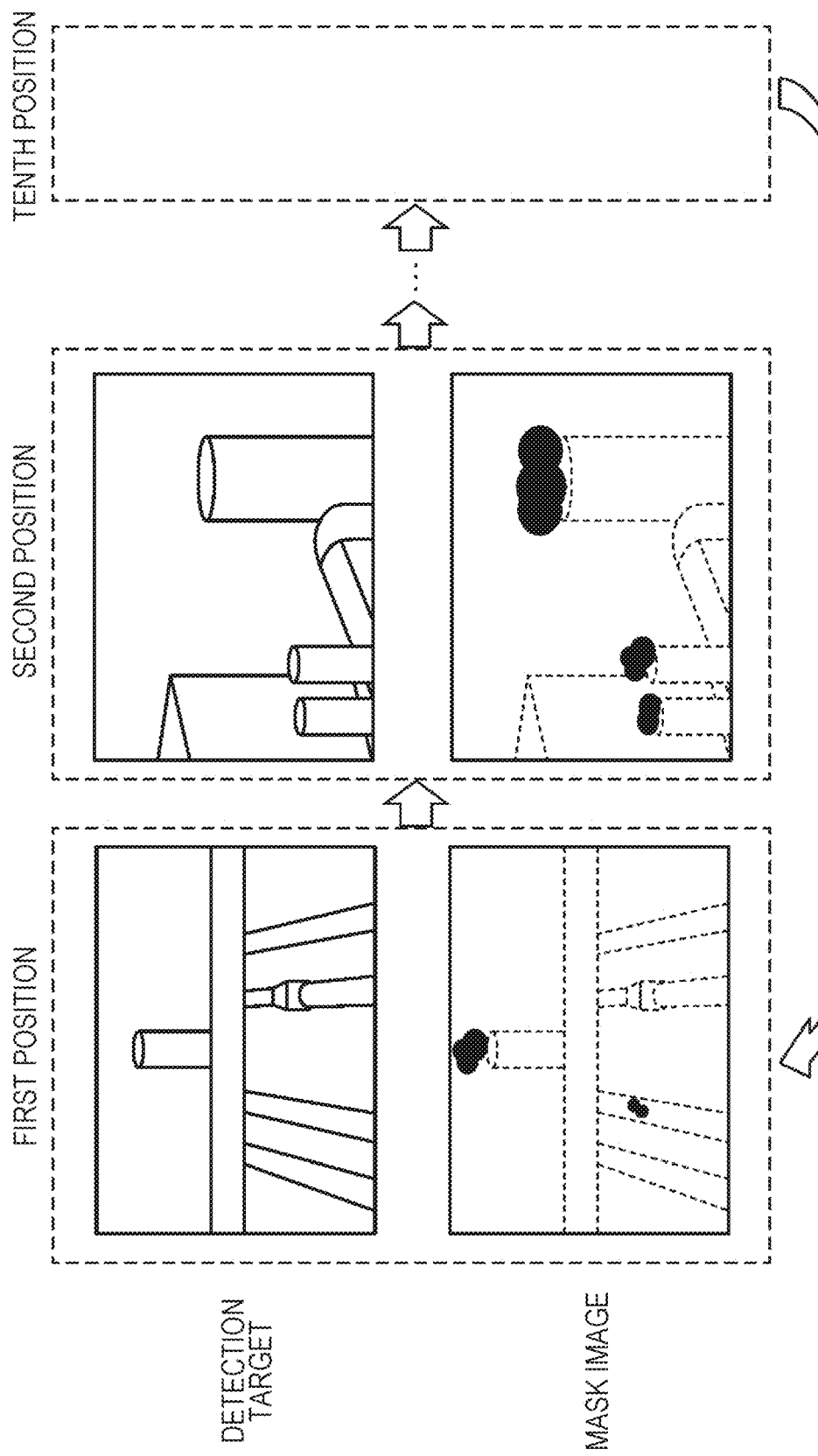

GAS DETECTION DEVICE, GAS DETECTION METHOD, AND GAS DETECTION PROGRAM

CROSS REFERENCE TO RELATED APPLICATIONS

This is the U.S. national stage of application No. PCT/JP2019/047950, filed on Dec. 6, 2019. Priority under 35 U.S.C. § 119(a) and 35 U.S.C. § 365(b) is claimed from Japanese Application No. 2019-050850, filed Mar. 19, 2019, the disclosure of which is also incorporated herein by reference.

TECHNICAL FIELD

The present invention relates to a gas detection device, a gas detection method, and a gas detection program for detecting gas present in a space.

BACKGROUND ART

Conventionally, a gas detection device that detects gas that is present in a space is known, and is disclosed in, for example, Patent Literature 1. An image processing device for gas detection disclosed in Patent Literature 1 is a device that performs image processing on infrared images of a gas-leak monitoring target captured at a plurality of time points. The image processing device includes an image processing unit that performs processing to remove, from image data representing the infrared images, second frequency component data having a lower frequency than that of first frequency component data, which represents temperature variations due to leaked gas, and representing temperature variations in a background of the monitoring target.

In a case where the gas detection device is used in order to perform predetermined work when gas is detected, if the gas detection is a false alarm, for example, a predetermined action for performing the predetermined work, such as preparation for performing the predetermined work or movement toward a place where the gas is detected, is to be wasted. Therefore, in order to reduce the false alarm, it is conceivable to use a mask that suppresses notification of detected gas even if the gas is detected. In a case of creating this mask, it is not necessarily clear which range in a detection range that can be detected by the gas detection device should be set as a mask range, and thus it is difficult to create the mask.

CITATION LIST

Patent Literature

Patent Literature 1: JP 6245418 B2 (WO 2017/073430 A)

SUMMARY OF INVENTION

The present invention has been made in view of the above circumstances, and an object thereof is to provide a gas detection device, a gas detection method, and a gas detection program capable of reducing the number of steps of creating a mask.

In order to achieve the object described above, a gas detection device, a gas detection method, and a gas detection program reflecting one aspect of the present invention are to detect gas on the basis of an image obtained by imaging a detection target. The gas detection device, the gas detection method, and the gas detection program: generate accumulated data obtained by accumulating a number of times of gas detection in a predetermined unit of accumulation, on the basis of a plurality of images captured at a plurality of times different from each other in a predetermined period; and generate a mask image for suppressing notification of detected gas on the basis of the generated accumulated data.

Advantages and features afforded by one or more embodiments of the invention are fully understood from the detailed description given below and the accompanying drawings. The detailed description and accompanying drawings are provided by way of example only, and are not intended as definitions of the limitations of the present invention.

BRIEF DESCRIPTION OF DRAWINGS

FIG. 5 is a view for explaining accumulation processing performed by the gas detection device.

FIG. 6 is a view for explaining the mask image generation processing performed by the gas detection device.

FIG. 10 is a view for explaining a relationship between an update timing of a mask image and an accumulation period of accumulated data.

FIG. 11 is a view for explaining a mask image edit screen implemented by the gas detection device.

FIG. 12 is a view for explaining a barycentric position of a gas region in a first modification.

FIG. 16 is a view for explaining a mask image in a third modification.

DESCRIPTION OF EMBODIMENTS

Figure 1:
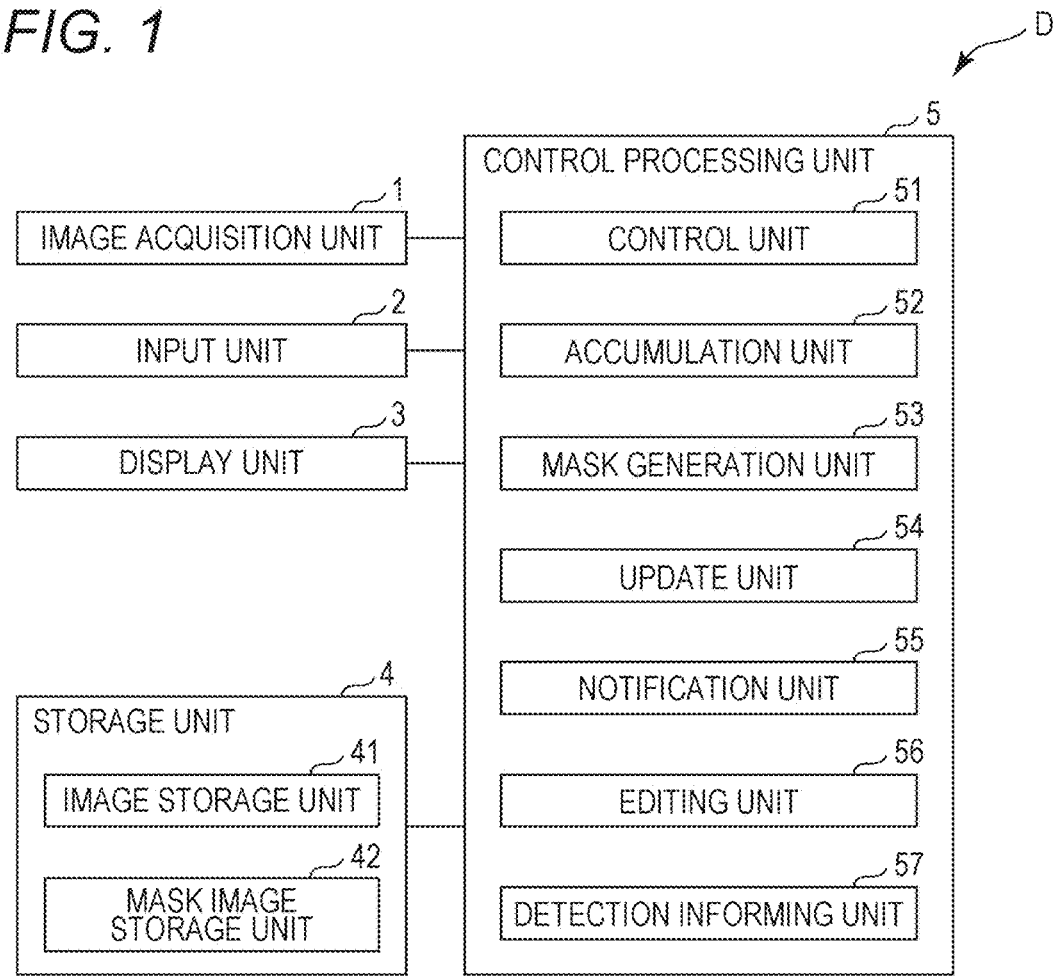
FIG. 1 is a block diagram showing a configuration of a gas detection device in an embodiment.

Hereinafter, one or more embodiments of the present invention will be described with reference to the drawings. However, the scope of the invention is not limited to the disclosed embodiments. Note that, in the individual drawings, the configurations denoted by the same reference numerals indicate the same configurations, and the description thereof will be appropriately omitted. In this specification, a generic term is indicated by a reference numeral with a suffix omitted, and an individual configuration is indicated by a reference numeral with a suffix.

A gas detection device according to an embodiment is a device that detects gas on the basis of an image obtained by imaging a detection target. Then, the gas detection device according to the embodiment includes: an accumulation unit that generates accumulated data obtained by accumulating a number of times of gas detection in a predetermined unit of accumulation, on the basis of a plurality of images captured at a plurality of times different from each other in a predetermined period; and a mask generation unit that generates a mask image for suppressing notification of detected gas on the basis of accumulated data generated by the accumulation unit. A more specific description will be given below.

FIG. 1 is a block diagram showing a configuration of the gas detection device in the embodiment. For example, as shown in FIG. 1, such a gas detection device D includes an image acquisition unit 1, an input unit 2, a display unit 3, a storage unit 4, and a control processing unit 5.

The image acquisition unit 1 is a device that is connected to the control processing unit 5 and acquires a plurality of images at a plurality of times (timings) different from each other in a predetermined period under the control of the control processing unit 5. The plurality of acquired images are stored in an image storage unit 41 in the storage unit 4 described later. A mask image is automatically generated by statistical processing as described later. Therefore, the predetermined period is an appropriate period (for example, 10 days, 20 days, 30 days, or the like) in which the generated mask image has statistical significance, and is set in advance. Further, in a case where the detection target is an outdoor facility, accuracy of the mask image is improved when the plurality of images are generated under various weather conditions such as clear sky, cloudiness, rain, different wind intensities and wind directions, and the like, and thus the predetermined period is preferably longer. The plurality of images may be, for example, an original image (source image) used for detecting gas. In this case, the image acquisition unit 1 is an infrared camera or the like that generates the original image, for example, an infrared image, and the control processing unit 5 generates a gas detection image indicating the presence or absence of gas for each pixel by any of various known gas detection methods. Alternatively, the plurality of images may be the gas detection image. In this case, the image acquisition unit 1 is a gas sensor or the like that captures an image of a detection target and generates a gas detection image by any one of various known gas detection methods.

Furthermore, for example, the image acquisition unit 1 may be an interface circuit that transmits and receives data to and from external equipment. In this case, the interface circuit acquires a plurality of original images or a plurality of gas detection images as the plurality of images, for example, from a recording medium (for example, a USB memory, a CD-ROM, a DVD-ROM, or the like) on which the plurality of original images or the plurality of gas detection images are recorded, or from a server device that manages the plurality of original images or the plurality of gas detection images. Even in this case, when the plurality of images is the plurality of original images, the control processing unit 5 generates the gas detection image by the any of the methods.

As the gas detection method, it is possible to use a known method such as, for example, a method disclosed in JP 5343054 B1 (JP 2012-058093 A), a method disclosed in WO 2017/073426 A, and a method disclosed in WO 2017/073430 A (Patent Literature 1 described above).

For example, the device disclosed in Patent Literature 1 first executes processing to remove second frequency component data having a lower frequency than that of first frequency component data, which represents temperature variations due to leaked gas, and representing temperature variations in a background of a monitoring target from an image data representing an infrared image. In this case, the image data is moving image data having a structure in which a plurality of frames are arranged in a time series, and the device sets, as time-series pixel data, data obtained by arranging, in time series, pixel data of pixels at the same position in the plurality of the frames, and performs processing to remove the second frequency component data on each of a plurality of pieces of the time-series pixel data constituting the moving image data. For the time-series pixel data, the device sets data extracted by performing first predetermined processing as the second frequency component data, and extracts a plurality of pieces of the second frequency component data respectively corresponding to a plurality of pieces of the time-series pixel data. The device sets, as first difference data, data obtained by calculating a difference between the time-series pixel data and the second frequency component data extracted from the time-series pixel data, and calculates a plurality of pieces of the first difference data respectively corresponding to a plurality of pieces of the time-series pixel data. The device sets, as first variation data, data representing variations of the first difference data calculated by performing a predetermined arithmetic operation on the first difference data in units of a second predetermined number of the frames, and calculates a plurality of pieces of the first variation data respectively corresponding to a plurality of pieces of the time-series pixel data. The first variation data is first fluctuation data, and the device obtains the first fluctuation data by calculating, for the first difference data, a moving standard deviation or a moving variance in units of the second predetermined number of the frames that are less than the plurality of frames. Then, the device detects the presence or absence of gas for each pixel by determining the first fluctuation data with a given threshold value.

The input unit 2 is, for example, equipment that is connected to the control processing unit 5, and inputs, to the gas detection device D, various commands such as a command for instructing a start of gas detection, and various data necessary for detecting gas, such as an input of an identifier in a detection target. For example, the input unit 2 is a plurality of input switches to which predetermined functions are assigned, a keyboard, a mouse, and the like. Then, in the present embodiment, the input unit 2 receives an editing operation for a mask image displayed on the display unit 3 as described later.

The display unit 3 is a device that is connected to the control processing unit 5, and displays a command and data inputted from the input unit 2, a mask image generated as described later, and the like under the control of the control processing unit 5, and is, for example, a CRT display, a liquid crystal display (LCD), an organic EL display, or the like.

The storage unit 4 is a circuit that is connected to the control processing unit 5, and stores various predetermined programs and various predetermined data under the control of the control processing unit 5. The various predetermined programs include: a control program that controls each of the units 1 to 4 of the gas detection device D in accordance with a function of each of the units; an accumulation program that generates accumulated data obtained by accumulating a number of times of gas detection in a predetermined unit of accumulation, on the basis of a plurality of images captured at a plurality of times different from each other in a predetermined period; a mask generation program that generates a mask image for suppressing notification of detected gas on the basis of accumulated data generated by the accumulation program; an update program that updates the mask image by causing the accumulation program to generate the accumulated data and causing the mask generation program to generate the mask image for each predetermined update period; a notification program that notifies the outside of first generation of the mask image and update of the mask image; an edit program that edits the mask image in accordance with an editing operation received by the input unit 2 and sets the edited mask image as a final mask image; and a control processing program such as a detection informing program that informs gas detection by using the mask image. The various types of predetermined data include data and the like necessary for executing each program such as, for example, a plurality of images acquired by the image acquisition unit 1, and a mask image generated on the basis of the plurality of images acquired by the image acquisition unit 1. The storage unit 4 includes, for example, a read only memory (ROM), which is a nonvolatile storage element, an electrically erasable programmable read only memory (EEPROM), which is a rewritable nonvolatile storage element, and the like. The storage unit 4 includes a random access memory (RAM) serving as a working memory, which stores data and the like generated during execution of the predetermined program, of the control processing unit 5. Note that the storage unit 4 may include a hard disk device having a relatively large storage capacity. Further, in the present embodiment, the storage unit 4 functionally includes the image storage unit 41 that stores the plurality of images acquired by the image acquisition unit 1, and a mask image storage unit 42 that stores a mask image generated on the basis of the plurality of images acquired by the image acquisition unit 1.

The control processing unit 5 is a circuit to control each of the units 1 to 4 of the gas detection device D in accordance with a function of each of the units, and generate a mask image. The control processing unit 5 is configured with, for example, a central processing unit (CPU) and its peripheral circuits. The control processing unit 5 functionally includes a control unit 51, an accumulation unit 52, a mask generation unit 53, an update unit 54, a notification unit 55, an editing unit 56, and a detection informing unit 57, by execution of the control processing program.

The control unit 51 is to control each of the units 1 to 4 of the gas detection device D in accordance with a function of each of the units, and control the entire gas detection device D.

The accumulation unit 52 is to generate accumulated data obtained by accumulating a number of times of gas detection in a predetermined unit of accumulation, on the basis of a plurality of images captured at a plurality of times different from each other in a predetermined period. In the present embodiment, the predetermined unit of accumulation is a gas region formed by integrating, into one, a plurality of pixels that are at positions adjacent to each other and where gas has been detected. Therefore, in the present embodiment, the accumulation unit 52 generates, as the accumulated data, gas region accumulated data obtained by accumulating the number of times of gas detection for the gas region each. As described above, in a case where the plurality of images are original images, the control processing unit 5 generates a plurality of gas detection images from the plurality of original images each, by using a predetermined gas detection method. Then, the accumulation unit 52 generates the gas region accumulated data by accumulating the number of times of gas detection for the gas region each, by using the plurality of gas detection images. Whereas, in a case where the plurality of images are the gas detection images, the accumulation unit 52 generates the gas region accumulated data by accumulating the number of times of gas detection for each gas region by using the plurality of gas detection images, as it is. In the present embodiment, an accumulation result is assigned to each pixel.

The mask generation unit 53 is to generate a mask image for suppressing notification of detected gas on the basis of accumulated data generated by the accumulation unit 52, in the present embodiment, on the basis of the gas region accumulated data. For example, the mask generation unit 53 compares, for each pixel, the number of times of gas detection with a predetermined first threshold value set in advance. Then, the pixel is set as a mask pixel when the number of times of gas detection is equal to or larger than the predetermined first threshold value as a result of this comparison, while the pixel is not set as a mask pixel when the number of times of gas detection is less than the predetermined first threshold value as a result of the comparison. That is, a pixel having the number of times of gas detection equal to or larger than the predetermined first threshold value is set as a pixel (mask pixel) for which gas detection is not to be notified even if the gas is detected in the pixel, and the mask image is one or more aggregates of such mask pixels. Note that, similarly to the gas region, a region formed by integrating a plurality of mask pixels at positions adjacent to each other into one can be defined as a mask region, and the mask image can also be defined as one or more aggregates of such mask regions. The predetermined first threshold value is, for example, appropriately set in advance from a plurality of samples, and is, for example, 0.1%, 0.05%, 0.01%, or the like in terms of appearance rate ((appearance rate)=(number of times of gas detection)/(total number of plurality of images)×100%). The mask generation unit 53 stores the generated mask image in the mask image storage unit 42.

The update unit 54 is to update the mask image by causing the accumulation unit 52 to generate the accumulated data and causing the mask generation unit 53 to generate the mask image, for each predetermined update period. The predetermined update period is appropriately set in advance in accordance with, for example, a specification of the gas detection device D, characteristics of a detection target, a surrounding environment of the detection target, and the like, and is, for example, the same as the predetermined period used for generating the accumulated data. Note that, of course, the predetermined update period may be different from the predetermined period. The update unit 54 stores the updated mask image in the mask image storage unit 42.

The notification unit 55 is to notify the outside of the first generation of the mask image and the update thereof. The notification unit 55 may perform the notification by, for example, buzzer sound, message sound, lighting of an indicator, or the like, but the notification is performed by displaying the mask image on the display unit 3 in the present embodiment.

The editing unit 56 is to edit the mask image in accordance with an editing operation received by the input unit 2, and set the edited mask image as a final mask image. The editing unit 56 stores the edited mask image in the mask image storage unit 42.

The detection informing unit 57 is to inform gas detection using the mask image. In the present embodiment, the detection informing unit 57 performs the informing by displaying, on the display unit 3, a gas detection image (gas detection image after mask processing) obtained by performing mask processing on the gas detection image as described later by using the mask image. In the present embodiment, as described later, the mask processing is processing of deleting an image detected as gas, in order not to notify of gas detection for the mask region.

The input unit 2, the display unit 3, the storage unit 4, and the control processing unit 5 in such a gas detection device D can be configured by, for example, a tablet computer, a notebook computer, or a desktop computer. Further, in a case where the image acquisition unit 1 is the interface circuit, the image acquisition unit 1 can also be configured by the computer.

Figure 2:
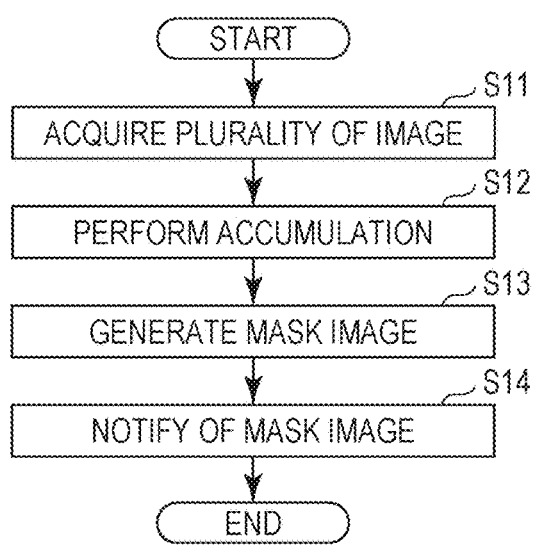
FIG. 2 is a flowchart showing an operation related to mask image generation processing in the gas detection device.
Figure 3:
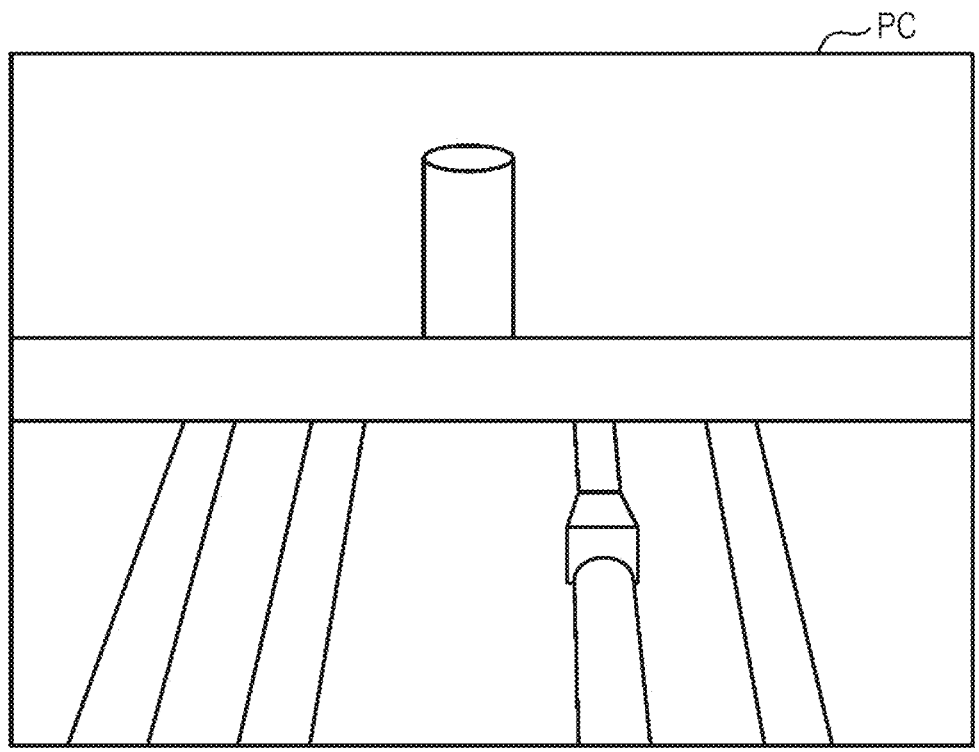
FIG. 3 is a view for explaining a visible image in a case where an image of a detection target is captured in a visible wavelength band, as an example.
Figure 4A:
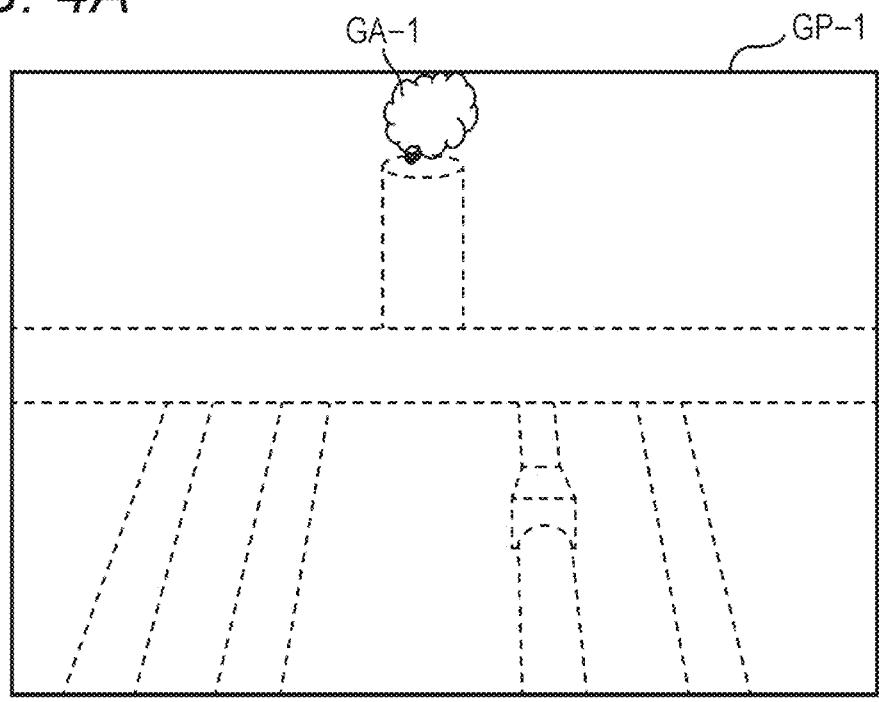
FIG. 4 is a view for explaining a gas detection image of a detection target, which is used in the gas detection device, as an example.
Figure 4B:
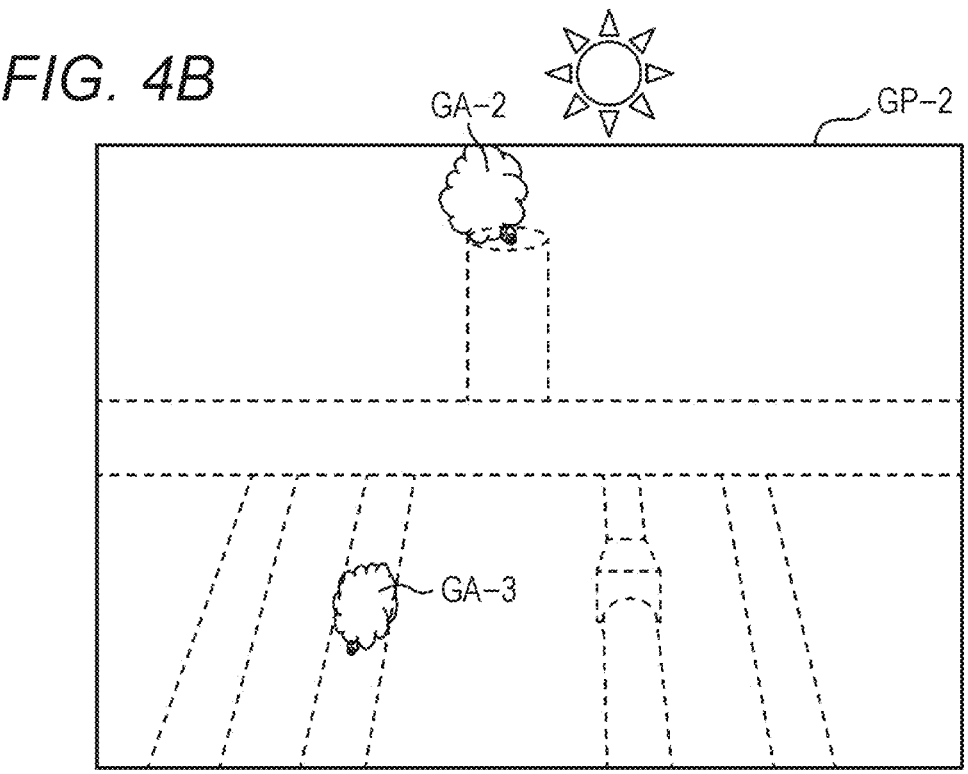
Figure 7:
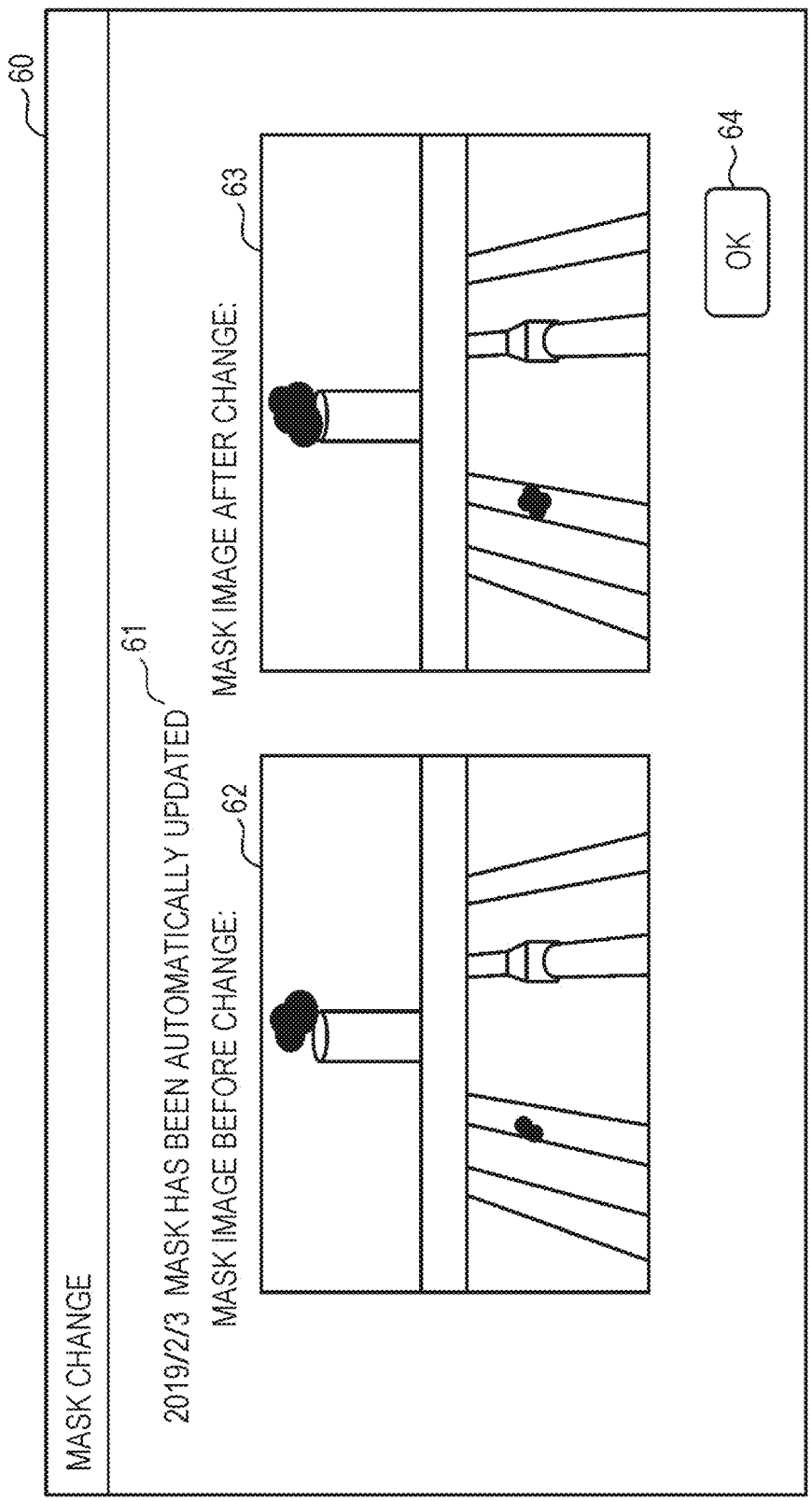
FIG. 7 is a view for explaining a mask image notification screen displayed by the gas detection device.

Next, an operation of the present embodiment will be described. FIG. 2 is a flowchart showing an operation related to mask image generation processing in the gas detection device. FIG. 3 is a view for explaining a visible image in a case where an image of a detection target is captured in a visible wavelength band, as an example. FIG. 4 is a view for explaining a gas detection image of a detection target, which is used in the gas detection device, as an example. FIG. 4A schematically illustrates a gas detection image that does not include an erroneously-detected gas region, and FIG. 4B schematically illustrates a gas detection image that includes an erroneously-detected gas region. FIG. 5 is a view for explaining accumulation processing performed by the gas detection device. FIG. 6 is a view for explaining the mask image generation processing performed by the gas detection device. FIG. 6A schematically illustrates an image of gas region accumulated data, and FIG. 6B schematically illustrates a mask image generated by threshold value determination processing. FIG. 7 is a view for explaining a mask image notification screen displayed by the gas detection device.

When the gas detection device D having such a configuration is powered on, the gas detection device D initializes each necessary unit and starts the operation. By execution of the control processing program, the control processing unit 5 functionally includes the control unit 51, the accumulation unit 52, the mask generation unit 53, the update unit 54, the notification unit 55, the editing unit 56, and the detection informing unit 57.

Then, for example, when an infrared camera, a gas sensor, or the like is newly arranged in order to monitor (surveillance) gas at a predetermined fixed position in a gas facility that handles gas, such as, for example, a gas storage, a gas power plant, and a gas plant, an operation of generating a mask image is started, for example, by receiving a predetermined command for instructing the input unit 2 to generate a new mask image, and the gas detection device D operates as follows regarding the mask image generation processing.

In FIG. 2, first, in the gas detection device D, the control processing unit 5 acquires, from the image acquisition unit 1, a plurality of images at a plurality of times different from each other in a predetermined period, and stores in the image storage unit 41 (S11). The plurality of images may be sequentially acquired and stored for each time of the generation over the predetermined period, for example. Alternatively, for example, the plurality of images may be accumulated in the image acquisition unit 1, and may be collectively acquired and stored after the lapse of the predetermined period. Alternatively, for example, the plurality of images may be acquired from a recording medium in which the plurality of images are recorded in advance or a server device that manages the plurality of images. As described above, the plurality of images may be original images or gas detection images. For example, for a detection target represented by an image PC in a visible wavelength band illustrated in FIG. 3, gas detection images GP-1 and GP-2 generated on the basis of an infrared image illustrated in FIGS. 4A and 4B are acquired. Note that the gas detection image GP does not include, for example, equipment (gas equipment) of a gas facility such as a pipe shown in FIG. 3, but the gas facility shown in FIG. 3 is illustrated by a broken line in FIG. 4 in order to easily grasp a corresponding positional relationship between FIGS. 3 and 4. The gas detection image GP-1 illustrated in FIG. 4A includes only a gas region GA-1 that is not erroneously detected, but the gas detection image GP-2 illustrated in FIG. 4B includes not only the gas region GA-2 that is not erroneously detected but also an erroneously-detected gas region GA-3 in which a shadow of the gas in the gas region GA-2 formed by solar radiation is detected as the gas. An object of the gas detection device D according to the present embodiment is to automatically generate a mask image for suppressing notification of gas detection in such an erroneously-detected gas region GA-3.

Next, in the gas detection device D, the accumulation unit 52 of the control processing unit 5 generates gas region accumulated data in which the number of times of gas detection is accumulated with the gas region as a unit of accumulation, on the basis of the plurality of images captured at the plurality of times different from each other in a predetermined period and acquired in process S11 (S12). For example, as shown in FIG. 5, when the number of times of gas detection image GP-1 including gas region GA-1 and the number of times of gas detection image GP-2 including gas regions GA-2 and GA-3 are accumulated for each gas region, the number of times of gas detection is accumulated as 2 in a gas region GA-12 where the gas region GA-1 overlaps with the gas region GA-2, and the number of times of gas detection in each pixel belonging to the gas region GA-12 is to be 2 in accordance with an accumulation result. In the gas region GA-1 and the gas region GA-2 excluding the overlapped gas region GA-12, the number of times of gas detection is accumulated as 1, and the number of times of gas detection in each pixel belonging to the gas region GA-1 and the gas region GA-2 excluding the overlapped gas region GA-12 is to be 1 in accordance with the accumulation result. The number of times of gas detection in the gas region GA-3 is accumulated as 1, and the number of times of gas detection in each pixel belonging to the gas region GA-3 is to be 1 in accordance with the accumulation result. As a result, an image SPa of the gas region accumulated data is generated as the accumulation result. Such accumulation processing is performed on the plurality of gas detection images GP, and as a result, for example, the image SPa of the gas region accumulated data illustrated in FIG. 6A is generated as a final accumulation result. Note that FIG. 6A illustrates a difference in the number of times of gas detection with a difference in hatching.

Next, in the gas detection device D, on the basis of the gas region accumulated data accumulated in process S12, the mask generation unit 53 of the control processing unit 5 generates a mask image for suppressing notification of detected gas and stores in the mask image storage unit 42 (S13). More specifically, the mask generation unit 53 compares, for each pixel, the number of times of gas detection with a predetermined first threshold value. Then, the pixel is set as a mask pixel when the number of times of gas detection is equal to or larger than the predetermined first threshold value as a result of the comparison, while the pixel is not set as a mask pixel when the number of times of gas detection is less than the predetermined first threshold value as a result of the comparison. In the present embodiment, since the predetermined first threshold value is expressed by an appearance rate, for example, the number of times of gas detection may be expressed by an appearance rate, and the comparison may be performed. Alternatively, for example, the predetermined first threshold value expressed by the appearance rate [%] may be expressed by the number of times by multiplying the appearance rate [%] by a total number of a plurality of images and dividing by 100, and the comparison may be performed. As a result, for example, a mask image MPa illustrated in FIG. 6B is generated from the image SPa of the gas region accumulated data illustrated in FIG. 6A. The image SPa of the gas region accumulated data illustrated in FIG. 6A includes an α region SA-1 including a plurality of pixels in which the number of times of gas detection is α, a β region SA-2 including a plurality of pixels in which the number of times of gas detection is β, and a γ region SA-3 including a plurality of pixels in which the number of times of gas detection is γ. When α>β (predetermined first threshold value)>γ, the α region SA-1 and the 13 region SA-2 become mask regions MK-1 and MK-2, respectively, while the γ region SA-3 does not form the mask region MK. As a result, the mask image MPa illustrated in FIG. 6B includes the mask regions MK-1 and MK-2.

Next, in the gas detection device D, the notification unit 55 of the control processing unit 5 displays, for example, the mask image accumulated in process S13 on the display unit 3 to notify the outside of the first generation of the mask image and the update thereof, here, of the first generation of the mask image, and ends the process (S14). For example, the notification unit 55 displays a notification screen 60 of the mask image illustrated in FIG. 7 on the display unit 3. The notification screen 60 of the mask image is a screen for notifying the user of the first generation of the mask image and the update thereof. More specifically, the notification screen 60 includes: a message region 61 that displays a message indicating that the first generation of the mask image or the update thereof has been performed; a pre-update mask image display region 62 that displays a pre-update mask image; a post-update mask image display region 63 that displays an updated mask image; and an "OK" button 64 for the user to input that the notification has been accepted. The message region 61 displays a generation date and a message such as "mask has been generated" in the first generation of the mask image, and displays an update date and a message such as "mask has been automatically updated" in the update of the mask image. The pre-update mask image display region 62 is blank in the first generation of the mask image. The pre-update mask image display region 62 is blank here although the mask image is displayed in FIG. 7.

By such an operation, the mask image is automatically generated first, and the generation is notified.

Figure 8A:
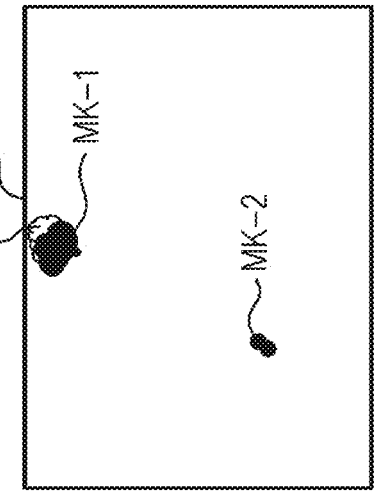
FIG. 8 is a view for explaining informing processing of gas detection using a mask image.
Figure 8B:
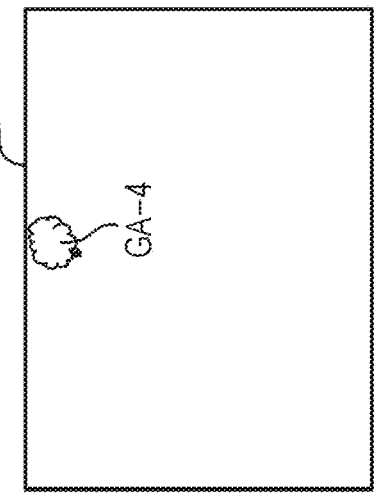
Figure 8C:
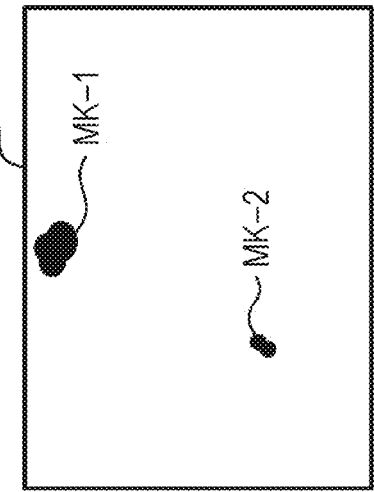
Figure 8D:
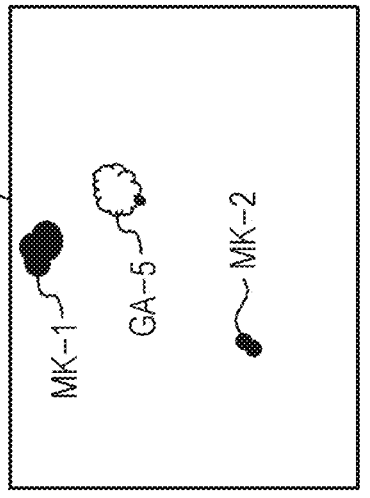
Figure 8E:
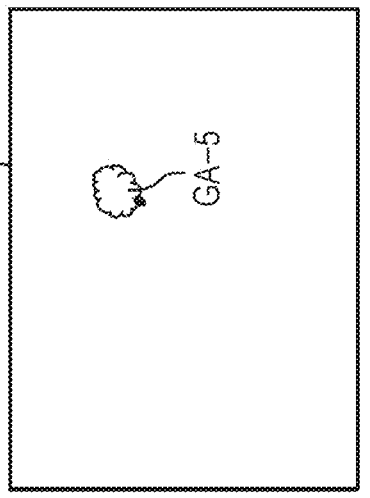

Next, the mask processing on the gas detection image using the mask image in this way will be described. FIG. 8 is a view for explaining informing processing of gas detection using a mask image. FIG. 8A schematically illustrates a mask image, FIG. 8B illustrates a gas detection image, FIG. 8C illustrates a case where gas detection is not notified by performing the mask processing on the gas detection image illustrated in FIG. 8B with the mask image illustrated in FIG. 8A, FIG. 8D illustrates a gas detection image, and FIG. 8E illustrates a case where gas detection is notified by performing the mask processing on the gas detection image illustrated in FIG. 8D with the mask image illustrated in FIG. 8A.

In a case of detecting gas in a detection target, the following operation is repeatedly performed at a predetermined sampling interval, and the detection target is monitored.

First, the gas detection device D acquires a current image from the image acquisition unit 1. When the current image is an original image as described above, the gas detection device D generates a current gas detection image from the current original image.

Next, in the gas detection device D, the detection informing unit 57 of the control processing unit 5 performs the mask processing on the current gas detection image by using a mask image, and generates a gas detection image after the mask processing. More specifically, first, the detection informing unit 57 determines whether or not a gas region indicating gas detection is included in the current gas detection image. In a case where the gas region is not included as a result of this determination, this processing is ended. Whereas, in a case where the gas region is included, the detection informing unit 57 retrieves (calls) a mask image stored in the mask image storage unit 42. For example, the mask image MPa illustrated in FIG. 8A is retrieved. Next, for each pixel belonging to the gas region, the detection informing unit 57 determines whether or not a pixel of the mask image at the same pixel position as a pixel position of the pixel is a mask pixel. As a result of this determination, the detection informing unit 57 deletes the gas region from the gas detection image when a ratio of pixels determined to be mask pixels is equal to or more than a predetermined second threshold value. Whereas, when the ratio of pixels determined to be mask pixels is less than the predetermined second threshold value, the detection informing unit 57 does not delete the gas region. In other words, for example, as shown in FIGS. 8C and 8E, the mask image MPa illustrated in FIG. 8A is superimposed on a gas detection image GP-3 illustrated in FIG. 8B so as to be at the same pixel position. Then, the gas region is deleted from the gas detection image when a ratio of the gas region overlapping with the mask region is equal to or more than the predetermined second threshold value, while the gas region is not deleted when the ratio of the gas region overlapping with the mask region is less than the predetermined second threshold value. For example, as shown in FIG. 8C, a gas region GA-4 in which the ratio is equal to or more than the predetermined second threshold value is deleted and is not notified, while, as shown in FIG. 8E, a gas region GA-5 in which the ratio is less than the predetermined second threshold value is notified without being deleted. For example, the predetermined second threshold value is appropriately set in advance from a plurality of samples, and is, for example, 65%, 70%, 75%, or the like in terms of an overlap ratio ((overlap ratio)=(area of gas region overlapping with mask region (number of pixels))/(area of gas region (number of pixels))×100%).

Next, when such mask processing is ended, the detection informing unit 57 performs informing of gas by displaying the gas detection image after the mask processing on the display unit 3.

The mask processing is performed by such an operation, and the gas detection is informed.

Figure 9:
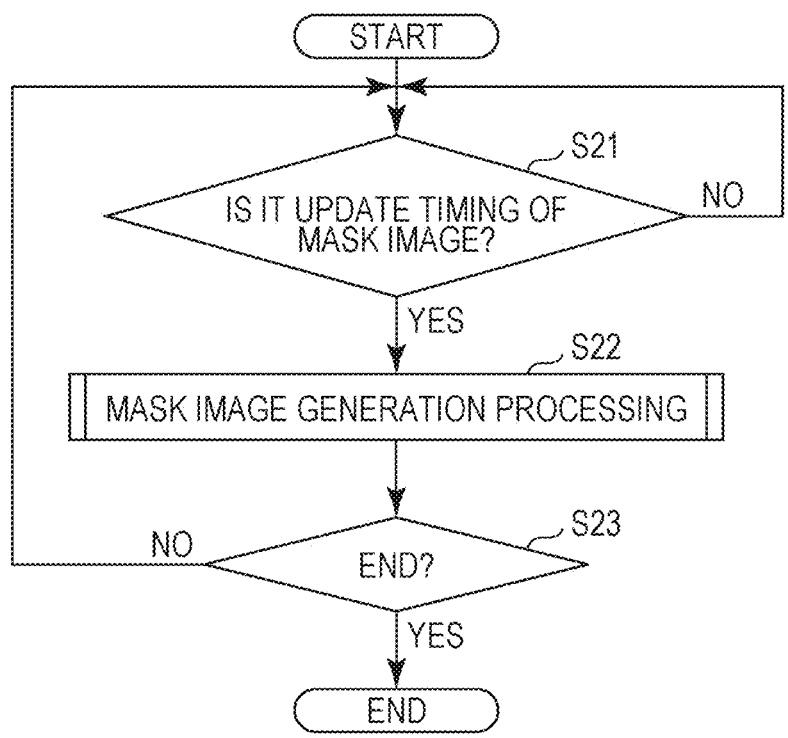
FIG. 9 is a flowchart showing an operation related to mask image update processing in the gas detection device.

Next, update of a mask image will be described. FIG. 9 is a flowchart showing an operation related to mask image update processing in the gas detection device. FIG. 10 is a view for explaining a relationship between an update timing of a mask image and an accumulation period of accumulated data. FIG. 10A illustrates a case of a first aspect, and FIG. 10B illustrates a case of a second aspect.

When the first mask image is generated and monitoring of a detection target is started, the gas detection device D determines whether or not it is an update timing of the mask image by the update unit 54 of the control processing unit 5 (S21). More specifically, the update unit 54 determines whether or not a predetermined update period has elapsed from the previous generation of the mask image (new generation or generation by update). As a result of this determination, in a case where it is the update timing (in a case where the update period has elapsed, Yes), the update unit 54 next executes process S22. Whereas, as a result of the determination, in a case where it is not the update timing (in a case where the update period has not elapsed, No), the update unit 54 returns the process to process S21. Therefore, in this case, the update unit 54 repeatedly executes process S21 until the update timing comes (until the update period elapses).

In process S22, the update unit 54 executes the mask image generation processing of causing the accumulation unit 52 to generate the accumulated data and causing the mask generation unit 53 to generate the mask image. Since this mask image generation processing is similar to the processes S11 to S14 described above with reference to FIG. 2, the description thereof will be omitted here. However, in the updating of the mask image, a period (used data period) for collecting the plurality of images (data of an original image or a gas detection image) used for updating the mask image may be the same as the update period as shown in FIG. 10A, or the used data period and the update period may not be the same as shown in FIG. 10B. For example, in the example illustrated in FIG. 10A, the used data period and the update period are the same 20 days, and a plurality of images collected in a period from a previous update timing to a current update timing are used for updating the mask image. For example, in update at an update timing T12, a plurality of images collected in a period from a previous update timing T11 to the current update timing T12 are used for updating the mask image. Further, for example, in the example illustrated in FIG. 10B, the used data period is 20 days and the update period is 10 days, and a plurality of images collected in the last 20 days at the current update timing are used for updating the mask image. For example, in the update at an update timing T23, a plurality of images collected in the last 20 days at the current update timing T23, that is, in a period from an update timing T21 that is before the last to the current update timing T23 are used for updating the mask image. In this way, in the example illustrated in FIG. 10B, some of the plurality of images used for updating the mask image at the previous update timing are used for updating the mask image at the current update timing. Therefore, continuity can be provided between the mask image before the update and the mask image after the update.

In process S23 subsequent to process S22, the gas detection device D determines whether or not an end of the operation is instructed by, for example, an input operation of a switch that turns on and off the operation. As a result of the determination, in a case where the end of the operation is instructed (Yes), the gas detection device D ends the present processing and ends the operation. Whereas, as a result of the determination, in a case where the end of the operation is not instructed (No), the gas detection device D returns the process to process S21. Note that, in a case where there is the input operation of the switch that turns on and off the operation while any one of the above-described process S21 and process S22 is being executed, the process being executed may be ended by the interruption, and the gas detection device D may end the operation.

Next, editing of the mask image generated first in this way and the mask image updated as described above will be described. FIG. 11 is a view for explaining a mask image edit screen implemented by the gas detection device.

For example, when the input unit 2 receives a predetermined command for instructing to edit a mask image, in the gas detection device D, the editing unit 56 of the control processing unit 5 displays, for example, a mask image edit screen 70 illustrated in FIG. 11 on the display unit 3. The mask image edit screen 70 is a screen for editing the mask image by deleting a mask pixel, adding a mask pixel, deleting a mask region, and adding a mask region on the mask image with a manual operation (editing operation) of the user received by the input unit 2. More specifically, the edit screen 70 includes: a mask image reference region 71 that displays a mask image stored in the mask image storage unit 42 for reference of the mask image before editing; a mask image editing region 72 that displays a mask image stored in the mask image storage unit 42 when the edit screen 70 is first displayed for reference of the mask image being edited, and displays the edited mask image when an editing operation is received; an "OK" button 73 for input of an instruction to confirm the mask image displayed in the mask image editing region 72 as a final mask image in the current editing and store the final mask image in the mask image storage unit 42; and a "Cancel" button 74 for input of an instruction to disable current editing and end the editing.

For example, in an editing operation of deleting a mask pixel, the user places a mouse cursor of a mouse as an example of the input unit 2 on a mask pixel desired to be deleted in the mask image displayed in the mask image editing region 72, and performs right-clicking of the mouse. When this editing operation is received, the editing unit 56 generates an edited mask image by changing a mask pixel corresponding to the position of the mouse cursor to a normal pixel that is not masked, and displays the edited mask image in the mask image editing region 72. Furthermore, for example, in an editing operation of adding a mask pixel, the user places a mouse cursor on a mask pixel desired to be added in the mask image displayed in the mask image editing region 72, and performs left-clicking. When this editing operation is received, the editing unit 56 generates an edited mask image by changing a pixel corresponding to the position of the mouse cursor to a mask pixel, and displays the edited mask image in the mask image editing region 72.

Further, for example, in an editing operation of deleting a mask region, the user places a mouse cursor on a mask region desired to be deleted in the mask image displayed in the mask image editing region 72, and performs right-clicking. When this editing operation is received, the editing unit 56 generates the edited mask image by changing each pixel belonging to the mask region corresponding to the position of the mouse cursor to each normal pixel that is not masked, and displays the edited mask image in the mask image editing region 72. Further, for example, in an editing operation of adding a mask region, the user traces, while holding left-clicking, a contour line of a mask region desired to be added in the mask image displayed in the mask image editing region 72 with a mouse cursor of the mouse, and releases the left-clicking. When this editing operation is received, the editing unit 56 generates an edited mask image by changing each pixel belonging to an inner region of the contour line traced by the mouse cursor to each mask pixel, and displays the edited mask image in the mask image editing region 72. By adding the mask region, for example, a region where detection is unnecessary such as sky can be set as the mask region. Furthermore, in the editing operation of adding a mask region, the mask region desired to be added may be designated by each vertex of a figure or may be designated by a diagonal line of a rectangle. In the example illustrated in FIG. 11, the mask image (see the left side of the sheet of FIG. 11) having mask regions MK-1 and MK-2 before editing is edited to a mask image in which the mask region MK-2 is deleted and mask regions MK-3 and MK-4 are added by the editing operation (see the right side of the sheet of FIG. 11).

Then, when an input operation is performed on the "OK" button 73, the editing unit 56 stores the mask image displayed in the mask image editing region 72 in the mask image storage unit 42. Accordingly, the gas detection device D uses the edited mask image hereinafter.

Whereas, when an input operation is performed on the "Cancel" button 74, the editing unit 56 ends the display of the edit screen 70, and displays a predetermined screen (for example, a home screen, a monitoring screen, or the like) on the display unit 3.

The mask image is edited by such an operation.

As described above, in the gas detection device D and the gas detection method and the gas detection program implemented on the gas detection device D according to the embodiment, accumulated data of the number of times of detection is generated from a plurality of images captured in a predetermined period, and, on the basis of the generated total data, a mask image that masks the image from the viewpoint of suppressing a false alarm is generated. The gas detection device D, the gas detection method, and the gas detection program described above automatically generate the mask image in this way, so that it is not necessary to recognize a range to be set in the mask, and man-hours for creating the mask can be reduced.

The gas detection device D, the gas detection method, and the gas detection program described above automatically update the mask image. Therefore, when there is a change in a detection target, such as, for example, a change (stop or restart) in an operation state of a facility that is a detection target, and a change in sunlight or a change in season due to expansion of the facility or a change in surroundings of the detection target, the change can be handled.

Since the gas detection device D, the gas detection method, and the gas detection program described above notify of the update, the user (operator) can recognize the update of the mask image.

Since the gas detection device D, the gas detection method, and the gas detection program described above can edit the automatically created mask image, the user can generate a more appropriate mask image according to the detection target.

The gas detection device D, the gas detection method, and the gas detection program described above can generate a mask image in which a range of a mask is set with a gas region as a unit of accumulation.

Note that, in the above-described embodiment, the number of times of gas detection is accumulated with the gas region as the unit of accumulation, but it is possible to appropriately change without limiting to this. For example, the number of times of gas detection may be accumulated with a barycentric position of a gas region as the unit of accumulation (first modification). Such a gas detection device D, gas detection method, and gas detection program can generate a mask image in which a range of a mask is set with a barycentric position of a gas region as the unit of accumulation.

Figure 13A:
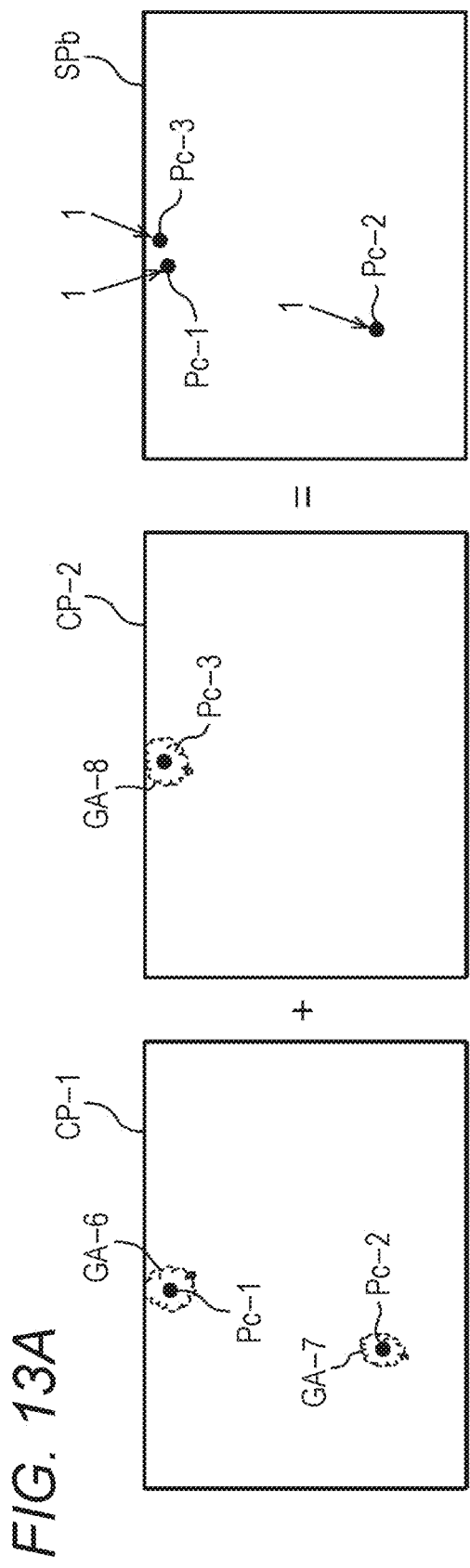
FIG. 13 is a view for explaining accumulation processing performed in the first modification and a mask image generated on the basis of a result of the accumulation processing.
Figure 13B:
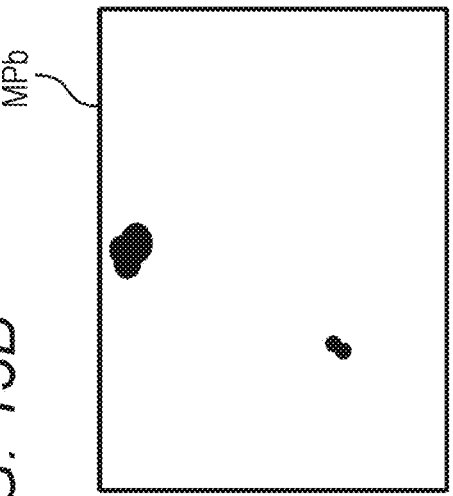
Figures 14A, 14B, 14C, 14D, 14E:
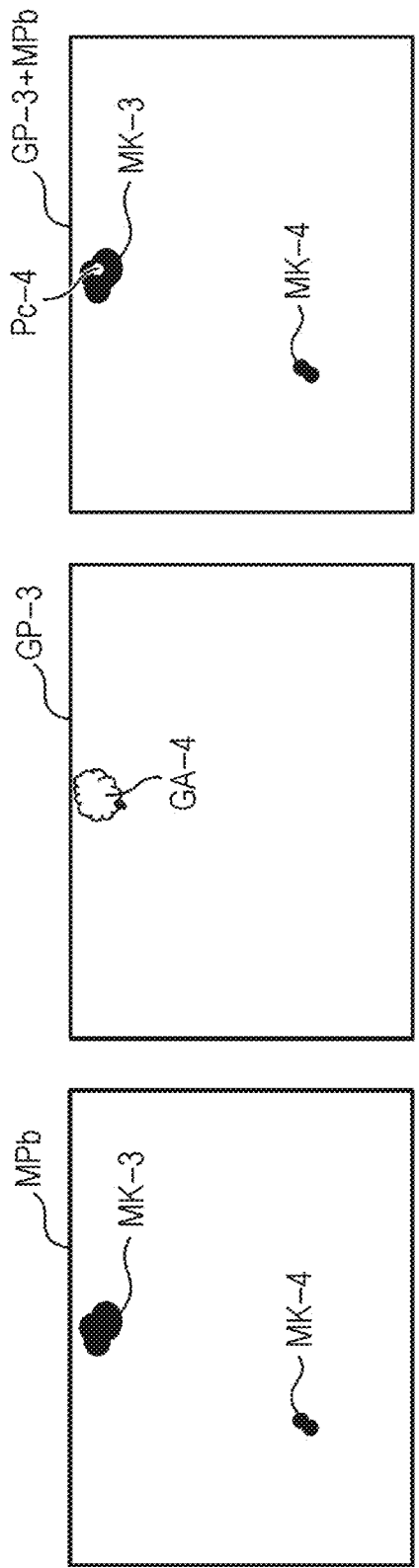
FIG. 14 is a view for explaining informing processing of gas detection using a mask image in the first modification.

FIG. 12 is a view for explaining a barycentric position of a gas region in the first modification. FIG. 12A schematically illustrates a gas detection image in which two gas regions are detected as an example, and FIG. 12B illustrates a barycentric position of each gas region illustrated in FIG. 12A. FIG. 13 is a view for explaining accumulation processing performed in the first modification and a mask image generated on the basis of a result of the accumulation processing. FIG. 13A is a view for explaining the accumulation processing in a case where a barycentric position is used as the unit of accumulation, and FIG. 13B is a view schematically illustrating a mask image in a case where the barycentric position is used as the unit of accumulation, as an example. Note that, in FIGS. 12B and 13A, a contour line of a gas region is indicated by a broken line. FIG. 14 is a view for explaining informing processing of gas detection using a mask image in the first modification. FIG. 14A schematically illustrates a mask image, FIG. 14B illustrates a gas detection image, FIG. 14C illustrates a case where gas detection is not notified by performing the mask processing on the gas detection image illustrated in FIG. 14B with the mask image illustrated in FIG. 14A, FIG. 14D illustrates a gas detection image, and FIG. 14E illustrates a case where gas detection is notified by performing the mask processing on the gas detection image illustrated in FIG. 14D with the mask image illustrated in FIG. 14A.

In this first modification, the accumulation unit 52 generates, as the accumulated data, barycentric position accumulated data in which the number of times of gas detection is accumulated for each barycentric position of a gas region. More specifically, first, the accumulation unit 52 obtains a barycentric position of a gas region for each of a plurality of gas detection images obtained at a plurality of times different from each other in the predetermined period. The barycentric position of the gas region is, for example, a coordinate average value, and an X coordinate is obtained by dividing the sum of X coordinate positions of all the pixels in the gas region by the number of pixels in the gas region, and a Y coordinate is obtained by dividing the sum of Y coordinate positions of all the pixels in the gas region by the number of pixels in the gas region. For example, in a case of a gas detection image GP-5 having gas regions GA-6 and GA-7 illustrated in FIG. 12A, a barycentric position Pc-1 of the gas region GA-6 and a barycentric position Pc-2 of the gas region GA-7 are obtained as shown in FIG. 12B. Note that the barycentric position of the gas region may be obtained by another calculation method without limiting to the above-described calculation method. Then, the accumulation unit 52 generates the barycentric position accumulated data by accumulating the number of times of gas detection at the barycentric position of the gas region obtained for each of the plurality of gas detection images. An accumulation result is assigned to each pixel. For example, as shown in FIG. 13A, for each barycentric position of a gas region, when the number of times of gas detection is accumulated for a gas detection image CP-1 including the gas region GA-6 with the barycentric position Pc-1 and the gas region GA-7 with the barycentric position Pc-2, and a gas detection image CP-2 including a gas region GA-8 with a barycentric position Pc-3, the barycentric positions Pc-1 to Pc-3 each do not overlap and are independent from each other, so that the number of times of gas detection at each pixel of each of the barycentric positions Pc-1 to Pc-3 is accumulated as 1. As a result, an image SPb of the barycentric position accumulated data is generated as the accumulation result.

The mask generation unit 53 generates a mask image on the basis of the barycentric position accumulated data and stores the mask image in the mask image storage unit 42. More specifically, similarly to the above-described embodiment, the mask generation unit 53 compares the number of times of gas detection with a predetermined first threshold value for each pixel at the barycentric position. Then, the pixel at the barycentric position is set as a mask pixel when the number of times of gas detection is equal to or larger than the predetermined first threshold value as a result of this comparison, while the pixel at the barycentric position is not set as a mask pixel when the number of times of gas detection is less than the predetermined first threshold value as a result of the comparison. As a result, for example, a mask image MPb illustrated in FIG. 13B is generated.

The detection informing unit 57 performs the mask processing on the gas detection image by using the mask image as follows, and performs the informing by displaying the gas detection image after the mask processing on the display unit 3. More specifically, first, the detection informing unit 57 determines whether or not a gas region indicating gas detection is included in the current gas detection image. In a case where the gas region is not included as a result of this determination, this processing is ended. Whereas, in a case where the gas region is included, the detection informing unit 57 retrieves a mask image stored in the mask image storage unit 42. For example, the mask image MPb illustrated in FIG. 14A is retrieved. Next, the detection informing unit 57 obtains a pixel at a barycentric position of a gas region, for each gas region included in the gas detection image. Next, for each gas region included in the gas detection image, the detection informing unit 57 determines whether or not a pixel at the barycentric position of the gas region is within a mask region, that is, whether or not the pixel is a mask pixel. As a result of this determination, the detection informing unit 57 deletes the gas region from the gas detection image when the pixel is within the mask region, and does not delete the gas region when the pixel is not within the mask region (when the pixel is outside the mask region). In other words, for example, as shown in FIGS. 14C and 14E, the mask image MPb shown in FIG. 14A is superimposed on the gas detection image GP-3 shown in FIG. 14B so as to be at the same pixel position. Then, a gas region GA-4 is deleted from the gas detection image GP-3 and is not notified when a barycentric position Pc-4 of the gas region GA-4 is within the mask region MK-3, while a gas region GA-5 is notified without being deleted when a barycentric position Pc-5 of the gas region GA-5 is not within the mask region.

Figure 15A:
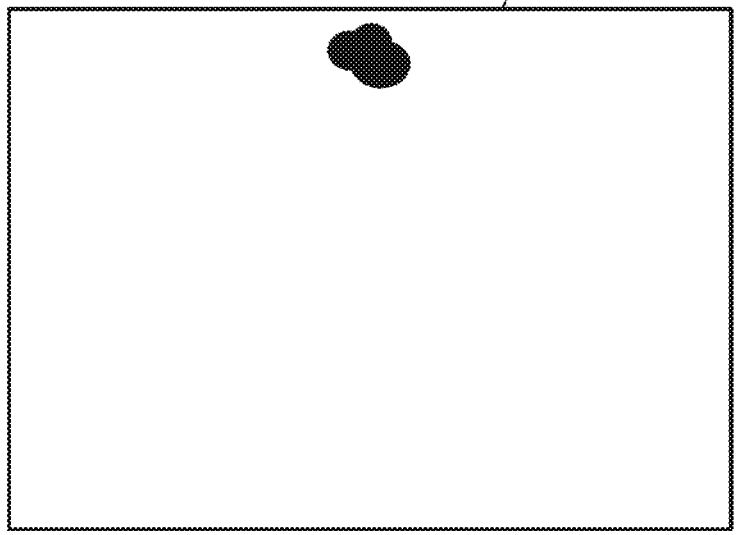
FIG. 15 is a view for explaining a mask image in a second modification.
Figure 15B:
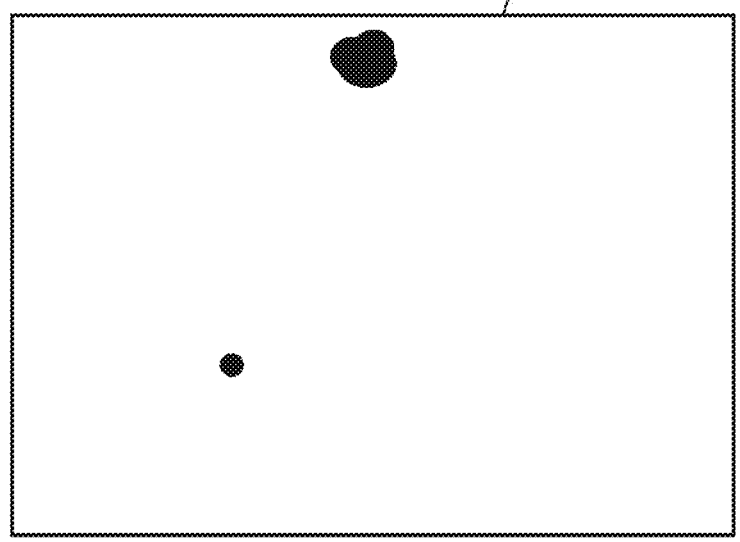

Further, in the above-described embodiment and the first modification thereof, the accumulation unit 52 may generate the accumulated data for each of a plurality of time zones different from each other, the mask generation unit 53 may generate the mask image for each of the plurality of time zones, and the detection informing unit 57 may perform the mask processing on a gas detection image by using a mask image in a time zone including an imaging time of the gas detection image and display the gas detection image after the mask processing on the display unit 3 (second modification). FIG. 15 is a view for explaining a mask image in the second modification. For example, a mask image MP-1 (MPa-1, MPb-1) in a time zone from 0 o'clock to 2 o'clock illustrated in FIG. 15A and a mask image MP-2 (MPa-2, MPb-2) in a time zone from 9 o'clock to 11 o'clock illustrated in FIG. 15B are generated. Of course, the mask image MP in another time zone may be generated. A change in the detection target includes a change according to a time zone, such as a change in a solar radiation direction with respect to the detection target. Such a gas detection device D, gas detection method, and gas detection program generate accumulated data for each of a plurality of time zones, and generate a mask image for each of the plurality of time zones. Therefore, it is possible to generate a more appropriate mask image according to the time zone.

Further, in the above-described embodiment and the first and second modifications thereof, the detection target may be a plurality of the detection targets different from each other, the accumulation unit 52 may generate the accumulated data for each of the plurality of detection targets, the mask generation unit 53 may generate the mask image for each of the plurality of detection targets, and the detection informing unit 57 may perform the mask processing on a gas detection image by using a mask image corresponding to the detection target of the gas detection image and display the gas detection image after the mask processing on the display unit 3 (third modification). FIG. 16 is a view for explaining a mask image in the third modification. For example, the mask image for a first position corresponding to a detection target of the first position is generated as shown in FIG. 16A, and a mask image for a second position corresponding to a detection target of the second position is generated as shown in FIG. 16B. For a detection target at another position, a mask image for the position is also generated. Since such a gas detection device D, gas detection method, and gas detection program generate the accumulated data for each of a plurality of detection targets, and generate the mask image for each of the plurality of detection targets, a more appropriate mask image corresponding to the detection target can be generated. In particular, when the plurality of images obtained by imaging individual detection targets at individual positions are generated by an imaging device having a pan-tilt function capable of changing an imaging direction in a left-right direction and an up-down direction and having a fixed installation position, the number of detection targets is often large in such an imaging device, and thus the third modification can be suitably used. Further, since the mask image can be automatically generated for each detection target, the third modification is effective in the above case.

As described above, this specification discloses various aspects of technology, of which the main technologies are summarized below.

A gas detection device according to one aspect is a device that detects gas on the basis of an image obtained by imaging a detection target, and includes: an accumulation unit that generates accumulated data obtained by accumulating a number of times of gas detection in a predetermined unit of accumulation, on the basis of a plurality of images captured at a plurality of times different from each other in a predetermined period; and a mask generation unit that generates a mask image for suppressing notification of detected gas on the basis of accumulated data generated by the accumulation unit.

Such a gas detection device generates accumulated data of a number of times of detection from a plurality of images captured in a predetermined period, and generates a mask image that masks the image from the viewpoint of suppressing a false alarm on the basis of the generated accumulated data. The gas detection device automatically generates the mask image in this way, so that it is not necessary to recognize a range to be set in the mask, and man-hours for creating the mask can be reduced.

In another aspect, the gas detection device described above further includes an update unit that updates a mask image by causing the accumulation unit to generate the accumulated data and causing the mask generation unit to generate the mask image, for each predetermined update period.

Since such a gas detection device further includes the update unit, when there is a change in a detection target, such as, for example, a change (stop or restart) in an operation state of a facility that is the detection target, and a change in sunlight or a change in season due to expansion of the facility or a change in surroundings of the detection target, the change can be handled.

In another aspect, the gas detection device described above further includes a notification unit that notifies the outside of update of the mask image.

Since such a gas detection device further includes the notification unit, the user (operator) can recognize the update of the mask image.

In another aspect, the gas detection device described above further includes: a display unit that displays the mask image; an input unit that receives an editing operation for a mask image displayed on the display unit; and an editing unit that edits the mask image in accordance with an editing operation received by the input unit and sets the edited mask image as a final mask image.

Since such a gas detection device can edit the automatically created mask image, the user can generate a more appropriate mask image according to the detection target.

In another aspect, in the gas detection device described above, the accumulation unit generates the accumulated data for each of a plurality of time zones different from each other, and the mask generation unit generates the mask image for each of the plurality of time zones.

A change in the detection target includes a change according to a time zone, such as a change in a solar radiation direction with respect to the detection target. Since the gas detection device generates the accumulated data for each of a plurality of time zones, and generates the mask image for each of the plurality of time zones, it is possible to generate a more appropriate mask image according to the time zone.

In another aspect, in these gas detection devices described above, the detection target is a plurality of detection targets different from each other, the accumulation unit generates the accumulated data for each of the plurality of detection targets, and the mask generation unit generates the mask image for each of the plurality of detection targets. Preferably, in the gas detection device described above, the plurality of images obtained by imaging the plurality of detection targets each are generated by an imaging device having a pan-tilt function and having a fixed installation position.

Since such a gas detection device generates the accumulated data for each of the plurality of detection targets, and generates the mask image for each of the plurality of detection targets, a more appropriate mask image corresponding to the detection target can be generated. In particular, in a case where the plurality of images are generated by the imaging device having a pan-tilt function capable of changing an imaging direction in a left-right direction and an up-down direction and having a fixed installation position, the gas detection device can be suitably used.

In another aspect, in the gas detection device described above, the predetermined unit of accumulation is a gas region formed by integrating, into one, a plurality of pixels that are at positions adjacent to each other and where gas has been detected, and the accumulation unit generates, as the accumulated data, gas region accumulated data obtained by accumulating the number of times of gas detection for the gas region each.

Such a gas detection device can generate a mask image in which a range of the mask is set with a gas region as the unit of accumulation.

In another aspect, in the gas detection device described above, the predetermined unit of accumulation is a barycentric position of a gas region formed by integrating, into one, a plurality of pixels that are at positions adjacent to each other and where gas has been detected, and the accumulation unit generates, as the accumulated data, barycentric position accumulated data in which the number of times of gas detection is accumulated for each barycentric position of the gas region.

Such a gas detection device can generate a mask image in which a range of the mask is set with a barycentric position of the gas region as the unit of accumulation.

A gas detection method according to another aspect is a method of detecting gas on the basis of an image obtained by imaging a detection target, and includes: an accumulation step of generating accumulated data obtained by accumulating a number of times of gas detection in a predetermined unit of accumulation, on the basis of a plurality of images captured at a plurality of times different from each other in a predetermined period; and a mask generation step of generating a mask image for suppressing notification of detected gas on the basis of accumulated data generated by the accumulation step. A gas detection program according to another aspect is a program for detecting gas on the basis of an image obtained by imaging a detection target, and is a program for causing a computer to execute: an accumulation step of generating accumulated data obtained by accumulating a number of times of gas detection in a predetermined unit of accumulation, on the basis of a plurality of images captured at a plurality of times different from each other in a predetermined period; and a mask generation step of generating a mask image for suppressing notification of detected gas on the basis of accumulated data generated by the accumulation step.

Such a gas detection method and gas detection program generate accumulated data of the number of times of detection from a plurality of images captured in a predetermined period, and generate a mask image that masks the image from the viewpoint of suppressing a false alarm on the basis of the generated accumulated data. The gas detection method and the gas detection program automatically generate the mask image in this way, so that it is not necessary to recognize a range to be set in the mask, and man-hours for creating the mask can be reduced.

This application is based on JP 2019-50850 A filed on Mar. 19, 2019, the contents of which are included in the present application.

Although the embodiment of the present invention has been illustrated and described in detail, it is merely illustration and an example, and not restrictive. The scope of the present invention should be construed by the language of the appended claims.

In order to express the present invention, the present invention has been appropriately and sufficiently described through the embodiment with reference to the drawings in the above description, but it should be recognized that those skilled in the art can easily modify and/or improve the above-described embodiment. Therefore, as long as the modifications or improvements made by those skilled in the art do not depart from the scope of the claims described in the claims, such modifications or improvements are to be construed as being within the scope of the claims.

INDUSTRIAL APPLICABILITY

According to the present invention, it is possible to provide a gas detection device, a gas detection method, and a gas detection program that detect gas present in a space.

The invention claimed is:

1. A gas detection device that detects gas based on an image obtained by imaging a detection target, the gas detection device comprising:
   a hardware processor that generates accumulated data obtained by accumulating a number of times of gas detection in a predetermined unit of accumulation, based on a plurality of images captured at a plurality of times different from each other in a predetermined period, and
   generates a mask image for suppressing notification of detected gas, based on accumulated data,
   wherein
   the predetermined unit of accumulation is a barycentric position of a gas region formed by integrating, into one, a plurality of pixels that are at positions adjacent to each other and where gas has been detected, and
   the hardware processor generates, as the accumulated data, barycentric position accumulated data in which the number of times of gas detection is accumulated for each barycentric position of the gas region.

2. The gas detection device according to claim 1, wherein the hardware processor updates the mask image by generating the accumulated data and the mask image, for each predetermined update period.

3. The gas detection device according to claim 1, further comprising:
   a display that displays the mask image; and
   an inputter that receives an editing operation for a mask image displayed on the display, wherein
   the hardware processor edits the mask image in accordance with an editing operation received by the inputter and sets the edited mask image as a final mask image.

4. The gas detection device according to claim 1, wherein the hardware processor generates the accumulated data for each of a plurality of time zones different from each other, and
   generates the mask image for each of the plurality of time zones.

5. The gas detection device according to claim 1, wherein the detection target is a plurality of the detection targets different from each other,
   the hardware processor generates the accumulated data for each of the plurality of detection targets, and
   generates the mask image for each of the plurality of detection targets.

6. The gas detection device according to claim 1, wherein the predetermined unit of accumulation is a gas region formed by integrating, into one, a plurality of pixels that are at positions adjacent to each other and where gas has been detected, and
   the hardware processor generates, as the accumulated data, gas region accumulated data obtained by accumulating the number of times of gas detection for the gas region each.

7. The gas detection device according to claim 2, wherein the hardware processor notifies an outside of update of the mask image.

8. The gas detection device according to claim 2, further comprising:
   a display that displays the mask image; and
   an inputter that receives an editing operation for a mask image displayed on the display, wherein
   the hardware processor edits the mask image in accordance with an editing operation received by the inputter and sets the edited mask image as a final mask image.

9. The gas detection device according to claim 2, wherein the hardware processor generates the accumulated data for each of a plurality of time zones different from each other, and
   generates the mask image for each of the plurality of time zones.

10. The gas detection device according to claim 2, wherein
    the detection target is a plurality of the detection targets different from each other,
    the hardware processor generates the accumulated data for each of the plurality of detection targets, and
    generates the mask image for each of the plurality of detection targets.

11. The gas detection device according to claim 2, wherein
    the predetermined unit of accumulation is a gas region formed by integrating, into one, a plurality of pixels that are at positions adjacent to each other and where gas has been detected, and
    the hardware processor generates, as the accumulated data, gas region accumulated data obtained by accumulating the number of times of gas detection for the gas region each.

12. The gas detection device according to claim 7, further comprising:
    a display that displays the mask image; and
    an inputter that receives an editing operation for a mask image displayed on the display, wherein
    the hardware processor edits the mask image in accordance with an editing operation received by the inputter and sets the edited mask image as a final mask image.

13. The gas detection device according to claim 7, wherein
    the hardware processor generates the accumulated data for each of a plurality of time zones different from each other, and
    generates the mask image for each of the plurality of time zones.

14. The gas detection device according to claim 7, wherein
    the detection target is a plurality of the detection targets different from each other,
    the hardware processor generates the accumulated data for each of the plurality of detection targets, and
    generates the mask image for each of the plurality of detection targets.

15. The gas detection device according to claim 7, wherein
    the predetermined unit of accumulation is a gas region formed by integrating, into one, a plurality of pixels that are at positions adjacent to each other and where gas has been detected, and
    the hardware processor generates, as the accumulated data, gas region accumulated data obtained by accumulating the number of times of gas detection for the gas region each.

16. A gas detection method for detecting gas based on an image obtained by imaging a detection target, the gas detection method comprising:
    generating accumulated data obtained by accumulating a number of times of gas detection in a predetermined unit of accumulation, based on a plurality of the images captured at a plurality of times different from each other in a predetermined period; and generating a mask image for suppressing notification of detected gas, based on accumulated data generated by the generating of accumulated data, wherein the predetermined unit of accumulation is a barycentric position of a gas region formed by integrating, into one, a plurality of pixels that are at positions adjacent to each other and where gas has been detected, and the hardware processor generates, as the accumulated data, barycentric position accumulated data in which the number of times of gas detection is accumulated for each barycentric position of the gas region.

17. A non-transitory recording medium storing a computer readable gas detection program for detecting gas based on an image obtained by imaging a detection target, the gas detection program causing a computer to execute:

generating accumulated data obtained by accumulating a number of times of gas detection in a predetermined unit of accumulation, based on a plurality of the images captured at a plurality of times different from each other in a predetermined period; and generating a mask image for suppressing notification of detected gas, based on accumulated data generated by the generating of accumulated data, wherein the predetermined unit of accumulation is a barycentric position of a gas region formed by integrating, into one, a plurality of pixels that are at positions adjacent to each other and where gas has been detected, and the hardware processor generates, as the accumulated data, barycentric position accumulated data in which the number of times of gas detection is accumulated for each barycentric position of the gas region.

* * * * *